United States Patent [19]

Goodman

[11] 4,048,558
[45] Sept. 13, 1977

[54] METHOD AND APPARATUS FOR DETECTING METAL FAILURES IN SITU

[76] Inventor: Clark Goodman, 95 Antigua Court, Coronado, Calif. 92118

[21] Appl. No.: 602,429

[22] Filed: Aug. 6, 1975

[51] Int. Cl.² .................................... G01R 27/00
[52] U.S. Cl. .................... 324/57 R; 324/57 Q; 324/57 SS; 324/58.5 A; 324/65 R; 324/DIG. 1
[58] Field of Search .............. 324/57 Q, 57 SS, 57 R, 324/58.5 A, 62, 64, 65 R, 40, 37, 1, 52, 61 QS, DIG. 1; 73/104

[56] References Cited

U.S. PATENT DOCUMENTS

| 2,150,922 | 3/1939 | Hay | 324/37 |
|---|---|---|---|
| 2,293,024 | 8/1942 | Klipsch | 324/1 |
| 2,304,739 | 12/1942 | Minton | 324/1 |
| 2,654,067 | 9/1953 | Bruce | 324/61 QS |
| 2,671,200 | 3/1954 | Lederer | 324/61 QS |
| 3,135,914 | 6/1964 | Callan et al. | 324/40 |
| 3,163,817 | 12/1964 | Simpson | 324/52 |
| 3,310,736 | 3/1967 | Bayly et al. | 324/62 R |
| 3,323,352 | 6/1967 | Branson | 324/61 QS |
| 3,340,466 | 9/1967 | Ono | 324/40 |
| 3,437,810 | 4/1969 | Wood et al. | 324/37 |
| 3,612,535 | 10/1971 | Davis | 324/DIG. 1 |
| 3,774,185 | 11/1973 | Parth | 324/61 QS |
| 3,818,758 | 6/1974 | Easter | 324/DIG. 1 |

FOREIGN PATENT DOCUMENTS 804,323 11/1958 United Kingdom .............. 324/65 R

OTHER PUBLICATIONS

New Crack Detector, Electrical Review, July 28, 1944, p. 125.

Primary Examiner—Stanley T. Krawczewicz
Attorney, Agent, or Firm—Kenyon & Kenyon, Reilly, Carr & Chapin

[57] ABSTRACT

Metal failures are detected in situ, for example, in the piping system of a nuclear reactor or a pipeline by passing a current through the metal in which the failures are to be detected at various frequencies and monitoring the impedance. By using various frequencies the present invention makes use of the skin effect thereby enabling, through detection of differences in impedance at different frequencies the determination of the depth of a crack or the like in the metal.

36 Claims, 10 Drawing Figures

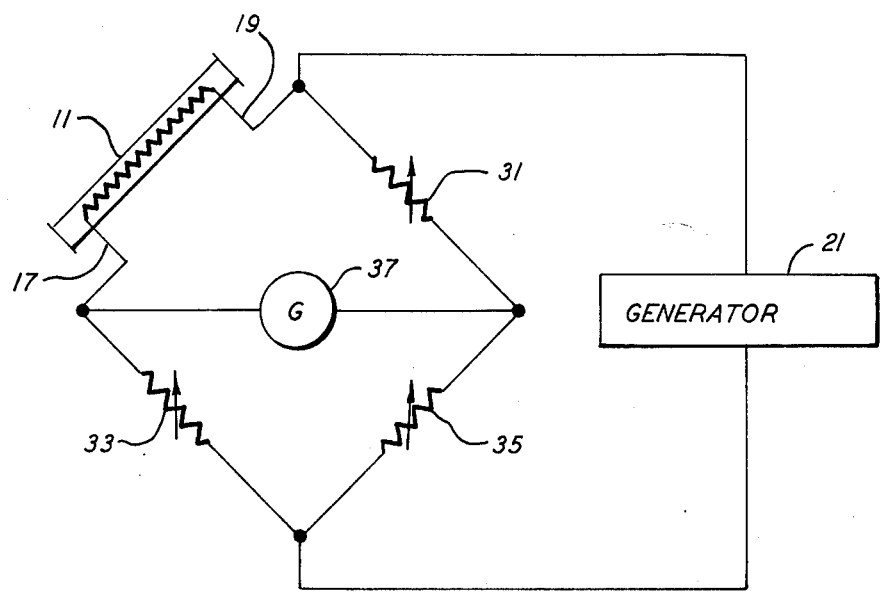
FIG. 2
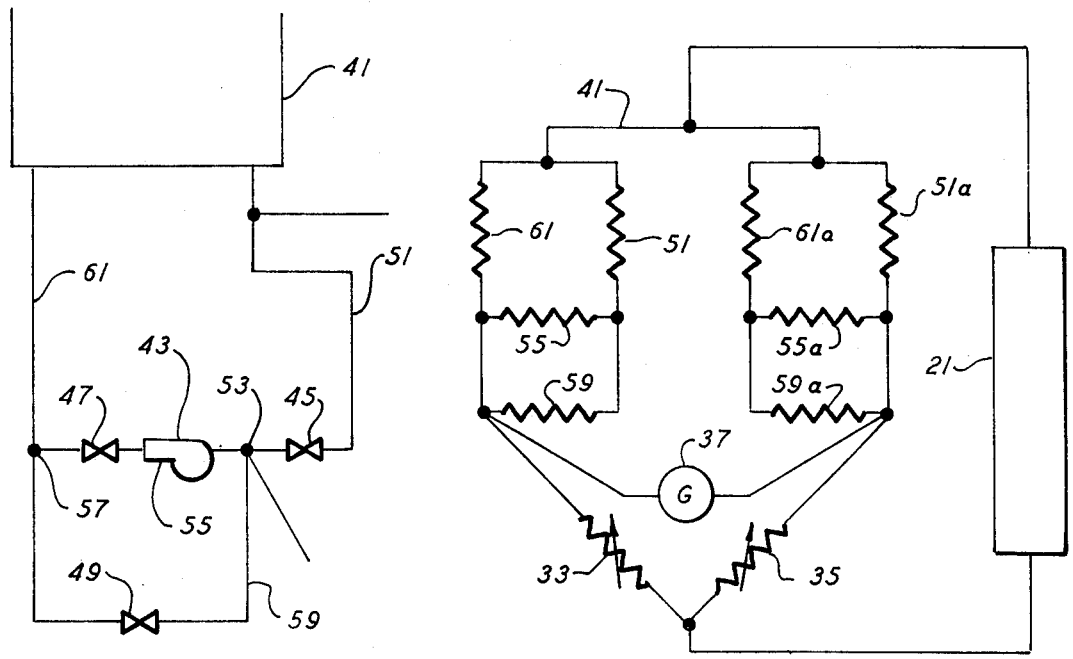
FIG. 3a
FIG. 3b

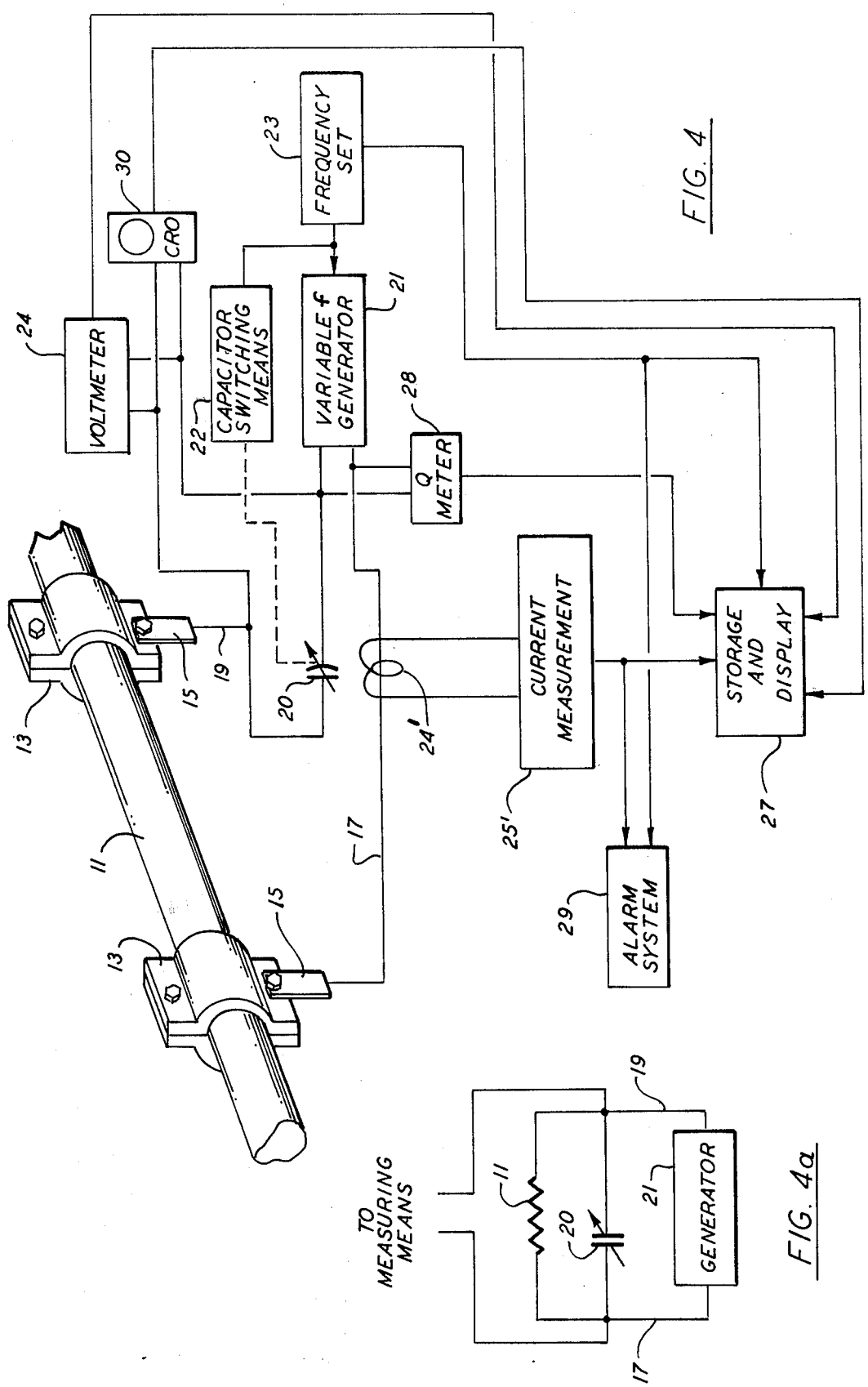

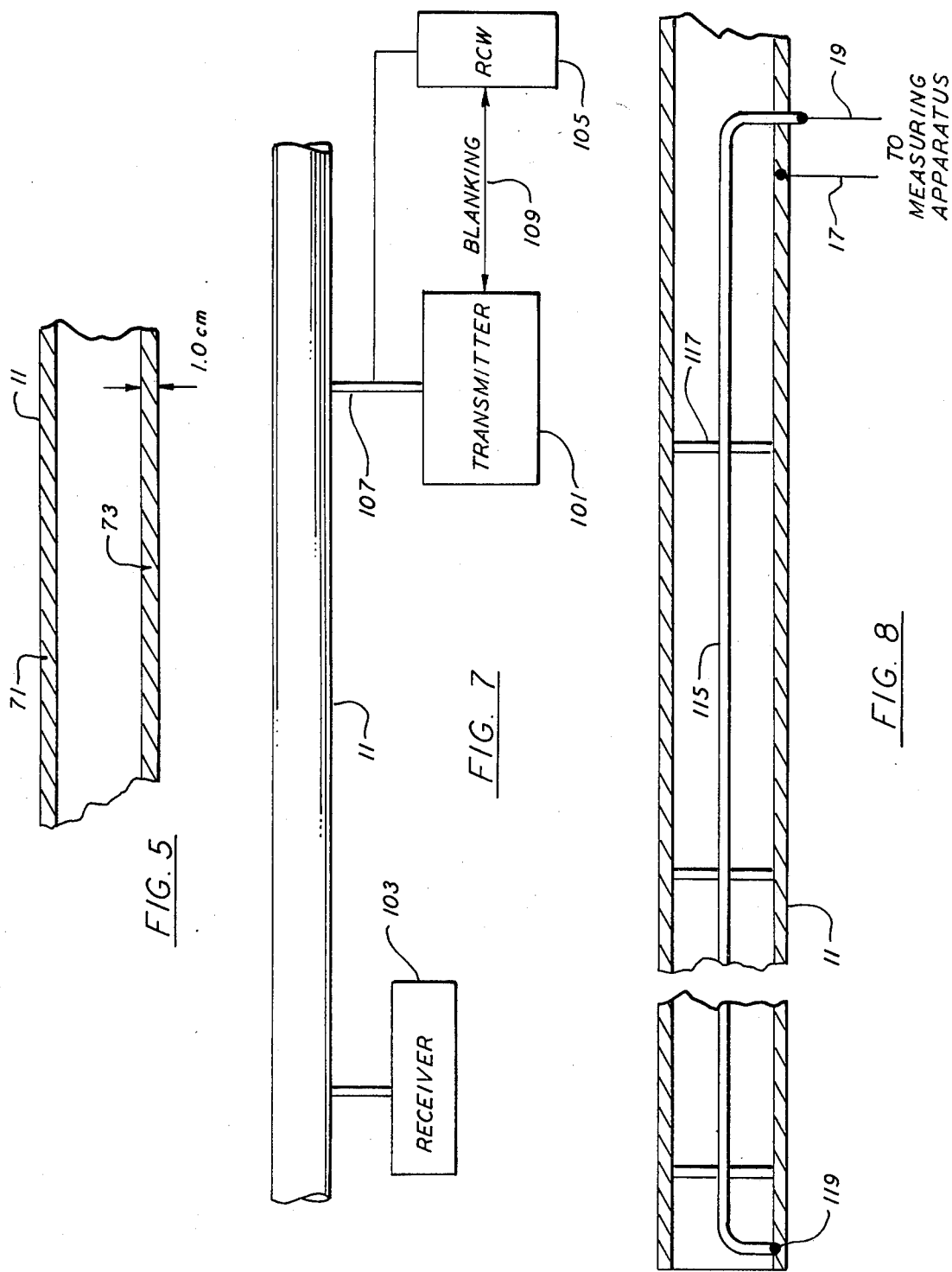

METHOD AND APPARATUS FOR DETECTING METAL FAILURES IN SITU

BACKGROUND OF THE INVENTION

This invention relates to a method and apparatus for detecting metal failures in general and more particularly to an improved method and apparatus of this type which permits making measurements of defects having a transverse component in situ.

Various electronic methods and apparatus for detecting metal failures have been developed. One known type induces eddy currents in the metal and includes means for determining the effect on those currents caused by cracks or other faults in the metal. Such a method, however, cannot reliably detect transverse defects. A second commonly used type is an acoustic type. Although, in many applications these types of measurements are adequate, there are certain areas where their use entails considerable expense.

An example of the problem which exists is the measurement of cracks in nuclear reactors. Quite recently twenty such reactors had to be shut down in order to carry out inspection of the piping in their emergency core cooling systems. Shut down was required since the present method being used, an ultrasonic method, requires that the reactors be shut down cooled and the insulation removed before the measuring equipment can be attached. Needless to say, such a shut down which can last a number of days entails great expense and results in a loss of the electric energy which would normally be generated by these reactors, thereby requiring other generating equipment to make up the loss or brown-outs in the community served.

There are other areas in which detection of faults in piping systems is of extreme importance. For example, six people were recently killed from $H_2S$ leakage from a pipe failure in a pectro-chemical plant.

From these two examples, it becomes evident there is a need for monitoring and detection equipment for defects having a transverse component which can operate in situ, without requiring a system shut down to avoid the occurrence of accidents and to avoid economic losses associated with shut downs for periodic inspection.

SUMMARY OF THE INVENTION

The present invention provides such a detection system. The present invention essentially comprises making measurements of an electrical characteristics of a circuit including a section of the metal structure at different applied frequencies. As the frequency of the applied electromotive force increases, the resulting electric current becomes concentrated more and more in the outer cross section of the metallic conductor. This phenomenon is what is commonly referred to as the skin effect and can be calculated quite precisely for simple geometric shapes. In complex systems the skin effect can be determined empirically when making impedance measurements at several different frequencies on a system which is known to be free of faults.

Through such measurements, it is possible to detect cracks and to follow their progress as they deepen. It is evident that because of the skin effect the impedance change resulting from cracks in the surface of the metal will be detected more readily if the electric current is being carried only by a surface layer of depth equal to or less than the depth of the crack. Since the skin depth varies at different frequencies, by monitoring the impedance at each of these frequencies the depth of a crack can readily be determined as long as it has a transverse component. i.e. a component normal to the direction of current flow.

In its simplest form, the present invention comprises means for generating a plurality of different frequencies and for applying them to a section of the metal to be detected. For example, in the case of a piping system the generator will be coupled through low impedance, large diameter copper wires or bus bars to low resistance copper couplings bolted to the piping. When used in a reactor or the like such connections can be put in place beneath the insulation so that removal thereof is not necessary for making measurements. In accordance with one embodiment of the present invention, the voltage drop across the piping section is measured to determine impedance.

A number of different manners of setting up the present invention are disclosed. Although the necessary impedance measurement can be simply done by using a digital voltmeter or the like, it is preferable that a system be constructed in which a bridge is used. The use of a bridge offers numerous advantages. In the first place, greater sensitivity can be obtained. Furthermore, the use of a bridge permits using two portions of the piping system as two bridge arms. This means that a reference arm of the bridge will be at essentially the same temperature as the section being measured. Since it is unlikely that cracks or faults will occur in both bridge arms at the same time, this still permits a reliable means of detecting cracks or the like in either arm. Furthermore, large sections of the piping system can be included in arms of the bridge. Branches of the piping system can simply be considered as branches of an impedance network. This makes it possible to map out the distribution of currents and potentials using well known principles of electric circuits, e.g. through the use of Kirchhoff's laws.

Also disclosed are a number of methods of making use of resonance in cases where the inductive reactance of the section of pipe being monitored is a factor. In such an embodiment capacitance is added in series or parallel with the circuit including the generator and the pipe line and adjusted to obtain resonance. By measuring changes in voltage, current or resonant frequency it is possible to detect the presence of cracks.

In addition to its use in piping systems in nuclear reactors and in chemical plants, the present invention can also be applied to long pipe lines. In such cases where the lengths of pipe which must be measured are large, it is preferred that an arrangement with a return conductor disposed inside the pipe line be used. In this case, the skin effect will take place at the inner surface of the pipe line where most defects are likely to occur because of the corrosive effects of the material within the pipe.

BRIEF DESCRIPTION OF THE DRAWINGS

FIG. 2 is a schematic diagram of a bridge arrangement for measuring impedance.

FIG. 3a illustrates a section of piping in a nuclear reactor.

FIG. 3b is a schematic diagram of the piping of FIG. 3a with the generator of the present invention attached.

FIG. 4 is a block diagram illustrating an embodiment of the present invention for operating in series resonance.

FIG. 4a is a schematic diagram of a portion of FIG. 4 arranged for parallel resonance.

FIG. 5 is a cross-section of a portion of pipe containing a crack.

FIG. 7 is a further embodiment of the present invention using a transmitter and receiver.

FIG. 8 is a schematic view of an alternate embodiment useful in pipelines.

DETAILED DESCRIPTION OF THE PREFERRED EMBODIMENT

Figure 1:
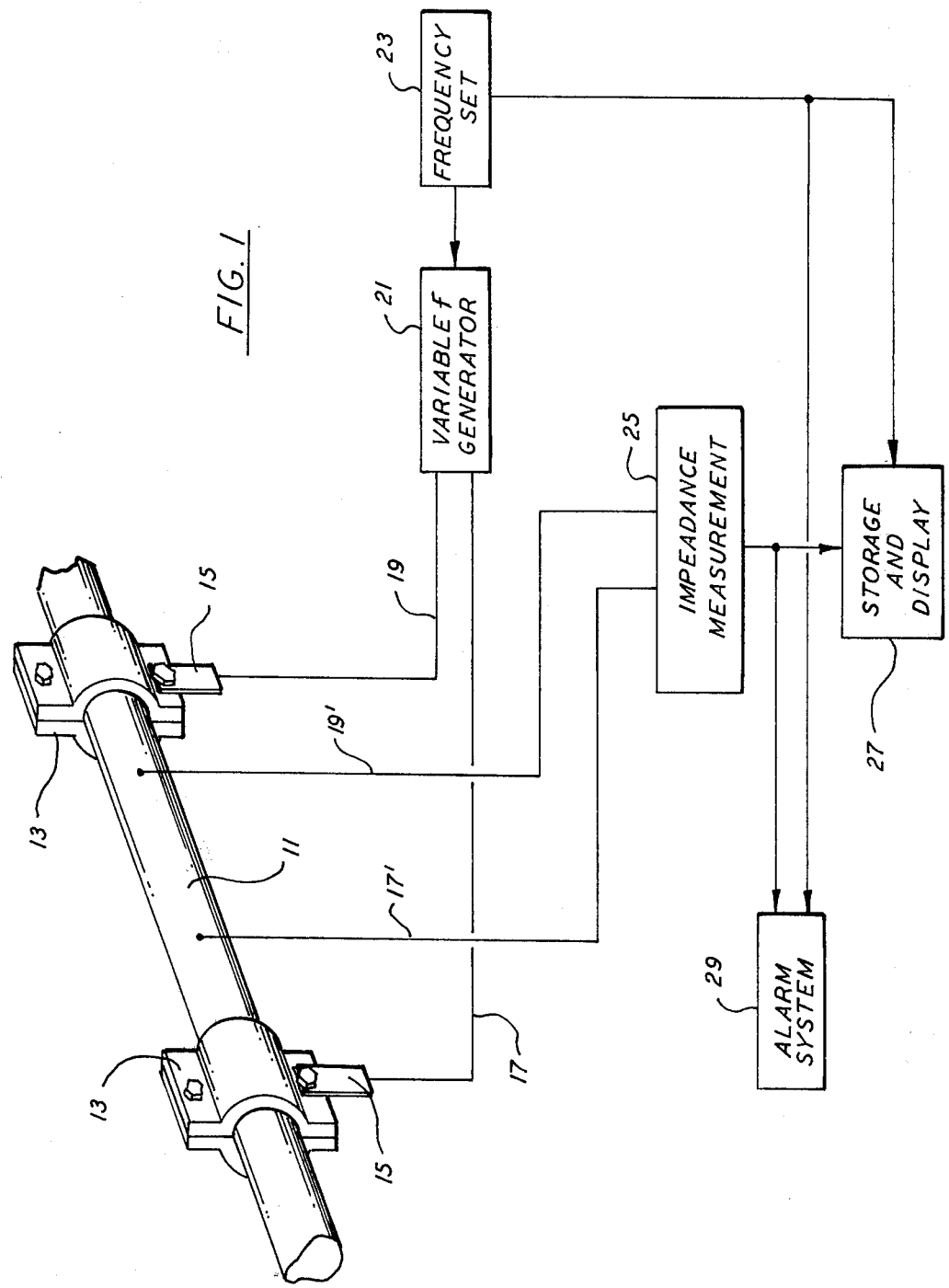
FIG. 1 is a block diagram illustrating an embodiment of the present invention for measuring impedance by measuring voltage drop.

FIG. 1 illustrates the basic elements in the present invention, partially in the perspective view and partially in the schematic view. Shown is a pipe or the like 11 which is to be tested for flaws, cracks and other defects. Clamped to the pipe in conventional fashion are two large clamping connections 13 preferably of low electrical resistance material such as copper. Terminal lugs 15 are connected to each of the connectors 13. The terminal lugs are connected by means of low resistance wires 17 and 19 to a variable frequency generator 21 whose frequency can be set by a frequency setting means 23. The frequency setting means may simply be a switch or the like used to provide switching inputs to the variable frequency generator to result in various frequency outputs. Attached through wires 17' and 19' is an impedance measurement device 25. In its simplest form this can comprise a digital voltmeter, although, as will be described more fully below, a bridge circuit is preferable. Where voltage alone is being used to measure the impedance, the variable frequency generator 21 will be controlled to provide an output which is a constant or known current. The output of the impedance measurement device 25 is provided to a storage and display device 27 and to an alarm system 29. Each of these two latter systems have an input from the frequency setting means 23. In operation, the operator can typically run through each of the frequencies using the frequency setting means 23. Alternatively, the frequency setting means 23 can be a stepper motor or the like to automatically step through preselected frequencies. The impedance is then measured at each frequency by the impedance measurement means 25 which provides an output proportional thereto to the storage and display 27. The simplest form of storage and display 27 would be a chart recorder. The input from the frequency setting means 23 may be used to switch between different channels on the recorder so the impedance for each frequency will be individually recorded. The output of the frequency setting means is also provided to the alarm system 29. The alarm system may comprise a plurality of comparators each having as a reference input a predetermined value above which there is likelihood a fault exists. The output of the frequency setting means 23 may be used to individually switch the output of the impedance measuring means to each of the comparators, one being associated with each frequency. Comparator outputs can then be provided as an input to an OR gate whose output drives a bell, light, etc.

It will be recognized that other types of storage and display means can be used. For example, the frequency setting means 23 and the storage and display means 27 can be included in a general purpose or special digital computer. In such a case, the comparisons required for providing an alarm could be carried out therein. The display could be in the form of a CRT display or printout. The computer clock could in that case be used to sequence through the various frequencies correlating the frequency being used with the impedance measured. Impedance measurements over a long period of time could be compared and averaged. Any deviation from the average value would indicate the possibility of a flaw, crack or the like and a suitable alarm output could be provided.

FIG. 2 illustrates an embodiment in which the impedance measurement is carried out using an impedance bridge. The section of pipe 11 provides one arm of the bridge. A variable reference impedance 31 provides a second arm of the bridge with additional variable impedances 33 and 35 providing the other ratio arms of the bridge. It is preferable that the impedance 31 simulate as closely as possible the impedance of the pipe 11. This may be accomplished in a number of ways. The impedance 31 may be enclosed within an oven whose temperature is closely controlled to simulate the temperature of the section of pipe 11. Or, rather than using a separate impedance 31 a dummy section of pipe may be used with that pipe maintained at a temperature equal to pipe 11. However, the most advantageous manner of providing such a reference is to use another section of pipe in the same system. As noted, the present invention is particularly applicable to nuclear reactors. The cooling liquid e.g. water or liquid sodium flowing through the piping will normally all be at the same temperature. Thus, by using two separate pipe sections an extremely good reference is obtained. Upon initial setup, the clamping connectors 13 shown on FIG. 1 can be adjusted on the piping so as to obtain equal impedances so that only a small amount of subsequent adjustment is required. Further balancing can be accomplished through the variable impedances 33 and 35. The bridge output is measured by a galvanometer 37 or the like. Preferably, digital instrumentation will replace a simple galvanometer so as to provide the capability of providing digital or analog outputs for use in a digital computer or on a chart recorder.

FIG. 3a illustrates a typical section of piping in a nuclear reactor. On this figure, 41 represents the reactor vessel. A recirculation pump 43 is shown with a suction valve 45 on one side and a discharge 47 on the other side. A bypass valve 49 is installed bypassing the pump 43 and the valve 47. In this arrangement there are thus a number of pipe branches. For example there is the branch 51 between the reactor and the junction point 53. Another branch is the branch 55 from junction point 53 to junction point 57. Another branch is the bypass branch 59. Finally, there is a branch 61 from the junction 57 back to the reactor 41. Each of these branches represents an impedance. Thus, the figure can be redrawn as shown on FIG. 3b showing the branches as impedances rather than branches. For this example, the impedance within the reactor will be considered as approaching zero because of the large path through which the current can flow. That is to say, the one end of the branch 61 and the branch 51 will both be essentially at the same point. Another similar branch exists at a different part of the reactor. This branch is shown next to the first branch with the same reference designations followed by an a. The two branches will have as a common point the reactor 41. These two may now be used as two arms of the bridge of FIG. 2 as illustrated on FIG. 3b.

lindrical pipes of various metals and dimensions as stated.

TABLE I

| (hz) | $\delta$ (Al) (cm) | $R_e$ (Al) ($\mu$ohm) | $\delta$ (Fe) (cm) | $R_e$ (Fe) ($\mu$ohm) | $\delta$ 20° C ($SS_a$) (cm) | $R_e$ 20° C ($SS_a$) ($\mu$ohm) | $\delta$ 800° C ($SS_a$) (cm) | $R_e$ 800° C ($SS_a$) ($\mu$ohm) |
|---|---|---|---|---|---|---|---|---|
| 0 | ∞ | 36 | ∞ | 130 | ∞ | 936 | ∞ | 1570 |
| 1 | 8.5 | 36 | 1.1 | 130 | 42.7 | 936 | 55.4 | 1570 |
| 9 | 2.8 | 36 | .37 | 336 | 14.2 | 936 | 18.5 | 1570 |
| 60 | 1.1 | 36 | .14 | 889 | 5.5 | 936 | 7.16 | 1570 |
| 400 | 0.43 | 80 | .055 | 2260 | 2.1 | 936 | 2.77 | 1570 |
| $10^4$ | 0.085 | 405 | .011 | .0113Ω | 0.43 | 2084 | 0.554 | 2714 |
| $10^5$ | 0.027 | 1280. | .0035 | .0356Ω | 0.135 | 6640 | 0.175 | 8590 |
| $10^6$ | 0.0085 | .0041Ω | .0011 | .113Ω | 0.043 | 0.021Ω | 0.0554 | 0.027Ω |
| $10^7$ | 0.0027 | .013Ω | $3.5 \times 10^{-4}$ | .356Ω | 0.0135 | 0.67Ω | 0.0175 | 0.086Ω |
| $10^8$ | 0.00085 | 0.041Ω | $1.1 \times 10^{-4}$ | 1.13Ω | .0043 | 0.208Ω | 0.00554 | 0.27Ω |

Symbols: f = frequency in hertz (hz) $\delta$ = skin depth in cm
R = effective resistance of pipe in ohm*
$\rho^t$ = resistivity in ohm-cm at temperature indicated ° C
l = length of pipe in cm
A = cross-section of metal in pipe in cm$^2$
$SS_a$ = austenitic stainless steel
Ω = ohm  $\mu$ohm = microohm  OD = outside diameter

*For comparison purposes each pipe is considered to be of length L = 1000 cm, OD = 25.4 cm, A = 76.6 cm$^2$. The resistivity values used are: $\rho$(Al) = 2.8 $\mu$ohm-cm at 20° C, $\rho$(Fe) = 10 $\mu$ohm-cm at 20° C, $\rho$($SS_a$) = 72 $\mu$ohm-cm at 20° C, $\rho$($SS_a$) = 121 $\mu$ohm-cm at 800° C.

It will be recognized that a compromise must be made between detection sensitivity and the length of pipe or number of branches which are monitored. Clearly, a crack will cause a greater fractional change in a short length of pipe of a single branch than in a long length of pipe or branch or a length with a number of branches. Furthermore, when branches such as shown on FIG. 3b are used the relative size of the crack as detected will depend upon which branch it is in. Thus, it will not be possible to directly obtain an indication of the crack size without knowing in which branch it is located. Were the arm of the bridge only a cross section of pipe as shown on FIG. 1, a direct indication of crack size would be available. However, even with an arrangement such as that shown on FIG. 3b changes will be evident. This, of course, is more important than knowing exactly where the crack is located or what size is the crack. Once a crack is detected, it will be monitored for changes. A crack which remains the same and does not migrate deeper can in some cases be ignored. However, if a significant change is detected either in magnitude or depth, shut down of the system may become necessary to locate and repair the crack.

The apparatus of the present invention can then be used to locate this crack. For this purpose, an arrangement such as that shown on FIG. 1 will be individually placed across branches such as the branches 51, 55, 59 and 61 of FIG. 3b until the section containing the crack is found. It is also possible to use other detection equipment in conjunction with that of the present invention for the final crack isolation. Previously, cracks in reactors have been detected by leakage of fluids or leakage of radioactive isotopes. The present invention in its ability to detect cracks as soon as they form should give an indication of a crack before such leakage occurs. However, it may also be used in conjunction with measurements made of fluid or radiation leakage in locating a crack. These two measurements together will go a long way toward isolating the location of the crack thus requiring only a small amount of insulation to be removed for the final check to be made. Furthermore, with the monitoring equipment of the present invention installed, the whole reactor need not be checked, only the sections indicating faults.

As noted above, the present invention relies upon the skin effect. Listed in Table I are the skin depths $\delta$ for various frequencies and the effective resistance for cylindrical pipes of various metals and dimensions as stated.

The length of pipe $l = 1000$ cm (32.8 feet), OD = 25.4 cm (10 inches), cross-sectional area of metal A = 76.6 cm$^2$ corresponding to a wall thickness of 1 cm. As an example consider an austenitic stainless steel ($SS_a$) pipe at 20° C with an applied frequencies of $10^4$ and $10^6$ hertz. The skin depths are 0.43 and 0.043 cm respectively. The corresponding effective resistances are 0.0021 and 0.021 ohm. A factor of 100 in frequency corresponds to a change in Re of a factor of ten.

The resistance of the pipe for dc and up to a frequency of 1600 hertz is 0.00094 ohms, substantially less than for higher frequencies.

Thus, at lower frequencies (below 1600 Hz) the ac resistance does not deviate appreciably from the dc resistance since the skin depth is equal to or greater than the wall thickness of the pipe. For example, assume generator 21 provides an output current of 50 amperes (rms) at a frequency of $10^5$ hertz. With reference to FIG. 2, and with the bridge balanced, the current will divide equally between the two branches so that 25 amperes will flow through pipe 11 and 25 amperes will flow through pipe 31. The resistance of each pipe will be 0.0066 ohm. The voltage drop across each pipe will be $25 \times 0.0066 = 165$ millivolt (rms). If the frequency increases to $10^6$ Hz the resistance essentially triples as does the voltage drop for the same current.

The piping section will of course have an inductance L. For a tube having inner and outer radii $r_1$ and $r_2$:

$$L = 0.002 \left[\ln \frac{2l}{r_1} + \ln \zeta - 1\right] \times l$$

where $l$ is the length of the tube, and $\ln \zeta$ is the geometric mean distance of an annulus. Values for this quantity have been tabulated in a book, "Inductance Calculations" by F. W. Groover, published by D. Van Nostrand Co., Inc. 1946 at page 23 designated as Table 4. For present purposes it need only be noted that the value of the term $\ln \zeta$ various between 0 and 0.25. The 0 condition comes about when the thickness becomes vanishingly small and the 0.25 value in the case of a solid rod. In examples given on page 36 of the above mentioned text, a tubular conductor 10 feet long with outer and inner diameters of 1 inch and 0.8 inches respectively is calculated to have an inductance of 3.19 $\mu$h. The limiting cases. i.e. where $\ln \zeta = 0$ and where $1n\zeta = 2.5$ are 3.153 µh and 3.306 µh, respectively. From this it can be seen that as the current begins to flow closer and closer to the surface of the pipe due to skin effect there will be little change in inductance due to this effect. In the limiting case, the case where $1n\zeta$ becomes 0, the value will be reduced from 3.19 to 3.153 µh. The inductance given above is for a nonmagnetic material, i.e. where $\mu = 1$. Magnetic materials do have a slightly different equation with the permeability having a slight effect. This term however is quite small and at high frequencies the same limiting equation as for nonmagnetic materials results. The inductive resistance $X_L$ of course is equal to $\omega L = 2\pi fL$ where $f$ is the frequency in Hertz and $\omega$ is angular frequency in radians per second.

The 10 foot long, 1 inch diameter pipe just mentioned, i.e. the example given in the aforementioned textbook, if made of austenitic stainless steel, would have the following values at 60Hz $$X_L = 2\pi fL = 120\pi \times 3.19 \times 10^{-6} = 0.0012 \text{ ohm}$$

$$R = \rho(SS_a)\frac{l}{A} = 72 \times 10^{-6}\frac{304.8}{1.824} = 0.012 \text{ ohm at } 20° \text{ C.}$$

It can be seen that in such a case the resistance is 10 times as great as the inductive reactance. At $10^5$ hertz $X_L$ increases to 2 ohm while the effective resistance only increases to $R = 0.022$ ohm because of the decreased effective cross-section of the tubular conductor. Thus, at higher frequencies the inductive reactance becomes much greater than the resistance. With the bridge arrangements of FIGS. 2 and 3 this is not of too great a significance. Through proper adjustment and selection of the ratio arms 33 and 35, for example, of FIG. 3b, it will still be possible to balance the bridge for each frequency. If necessary, an additional variable resistance or inductance can be placed in series with one of the other arms to aid in balancing. There may be a decreased sensitivity because of the fact the change due to the crack will primarily be a change in resistance rather than inductance. However, if the instrument 37 is of sufficient sensitivity changes will still be detectable. However, in a measuring scheme such as that shown on FIG. 1, some difficulties may be encountered. The current flowing through the pipe will be limited primarily by the inductive reactance. As a result the voltage drop across the pipe resulting from a small change in resistance may be more difficult to detect. In such cases, the present invention makes use of resonance. In the example give above at $10^5$ hertz the desired resonance frequency $$\omega_0 = \sqrt{1/LC} \text{ or } 2\pi \times 10^5 \text{ Hz}$$

$$C = \frac{1}{\omega_0^2 L} = \frac{1}{(2\pi 10^5)^2 \times 3.19 \times 10^{-6}} = 0.8 \text{ microfared}$$

A capacitor of this size is quite reasonable and feasible for insertion into a circuit such as that of FIG. 1.

FIG. 4 illustrates such an arrangement. Parts which are the same as those of FIG. 1 are given identical reference numerals. Thus, there is shown a similar arrangement including connections to the pipe section 11 with a variable frequency generator 21 and frequency setting means 23. However, in the line between the variable frequency generator and the pipe 11, a variable capacitor 20 is inserted. Variable capacitor 20 may be a capacitor which is continuously variable or may comprise a plurality of individual capacitors with means to switch them. Shown is a block labeled capacitor switching means 22 which also obtains an input from the frequency setting means and is used to control the capacitor. Such may comprise a servo system for driving a variable capacitor or may comprise a plurality of semiconductor or relay switches for individually switching in different capacitors in response to outputs from the frequency setting means 23. In its simplest form the means 22 may be a control knob for an operator to adjust. The arrangement shown is one for series resonance. FIG. 4a shows how capacitor 20 can instead be placed across the lines 17 and 19 to obtain parallel resonance with the inductive impedance of pipe section 11.

An example was given above of a 1,000 centimeter long pipe with an outer diameter of 25.4 centimeters. This is thought to be typical of the type found in nuclear reactors. For that pipe $l = 1,000$ cm, $r_1 = 12.7$ cm and $r_2 = 11.7$ cm. Using the equations given above, $L = 8.1$ microhenries, and $X_L = 0.0031$ ohm at 60 hertz and 5.1 ohm at $10^5$ hertz. $R_e$ at 20° C = 0.000936 ohm at 60 hertz and 0.00664 ohm at $10^5$ hertz. At $10^5$ hertz C would be equal to 0.31 microfarads to obtain resonance. In either of the examples given a high figure of merit, Q is obtained. Q equals $X_L/R$ and for the first example given with the 1 inch pipe would have a value of 167 at the $10^5$ hertz. For the second example given with the 10 inch pipe $Q_o$ would equal 768. In a series resonance circuit, $X_L = X_C$. Reactance becomes zero and current becomes a maximum and is limited only by the resistance R in the circuit. The figure of merit indicates how fast the current drops off from this maximum point. In a parallel resonance circuit when $X_L = X_C$ a maximum voltage is obtained with a large current circulating between the resistance and capacitance.

In the arrangement shown on FIG. 4, means 24 for measuring the voltage drop across capacitor 20 and means 25' for measuring current and obtaining an input from a current transformer 24' are shown. During initial setput, the capacitor to be switched in at each frequency can be trimmed to achieve maximum current and the maximum current value recorded. At resonance the voltage across capacitor 20, measured by voltmeter 24 will also be a maximum. Thereafter, when monitoring, the voltage and current values obtained can be compared with the maximum currents and voltages previously recorded. As with the previous embodiment these measured values can be stored and displayed and used to compare with the stored previous value to operate an alarm 29.

In addition to using an ammeter type device for measuring and recording the current through the pipe at a given frequency or over a range of frequencies other types of meters can also be used. For example, a Q meter 28 which measures the Q of the circuit can be used as well as a Cathode Ray Oscilloscope 30. Furthermore, outputs of these instruments can be recorded in a manner similar to that described above. If desired the various types of instruments may be provided with switches for coupling to Storage and Display means 27.

Alternatively, the frequency of the variable frequency generator using frequency setting means 23 can be scanned for each of a plurality of different capacitors or capacitor 20 trimmed for each of a plurality of frequencies and the current and voltage recorded during the scanning. The peak current and voltage will indicate the point of resonance. Any deviation in voltage or current peak amplitude or frequency at resonance will indicate a change in the impedance in the pipe. It should be noted that with a crack not only will the resistance change but small changes in inductance and capacitance can take place. Such can occur particularly in a ferromagnetic pipe. Because of the Q of the circuits and the sharpness of resonance the small changes will show up and can be detected by a shift in the resonance frequency of the circuit.

FIG. 5 illustrates a cross section of pipe 11 of FIGS. 1 and 2. Assume that a small crack 71 begins to form in the outer surface of the pipe. Also assume that the depth of this crack is 0.0135 centimeters. With reference to Table I, it will be seen that this corresponds for $SS_a$ at 20° C to the skin depth at $10^7$ Hz. At frequencies below that value, the crack will have minimal effect. The measured impedances will be very close to what they would be without the crack since a substantial portion of the current is flowing below the crack. However, when the frequencies reaches $10^7$, a considerable change can be expected in the measured impedance since the crack is in the area where most of the current must flow. By monitoring these changes it is possible then to gain an indication of the crack depth.

Although normally cracks begin from the outside and work in, the possibility of an internal crack exists. Such a crack, 73 in FIG. 5, can also be determined. Any crack will effect the dc resistance of the pipe section. Thus, the generator 21 can be operated at a dc or a very low frequency. Detection of a change at this frequency indicates only that a crack is present. Thereafter, the frequencies can be scanned. If the crack is on the inside, the opposite of what occurs for an external crack will happen. That is to say, at low frequencies there will be an increase in relative impedance but at higher frequencies where the current is flowing near the skin, the impedance will be normal since the current is not flowing through the crack. Thus, a measurement showing an increase in impedance with dc or a low frequency but showing normal impedance at higher frequencies indicates an inside crack. The depth of the crack can also be determined by determining at what point the impedance is no longer effected. As noted above, the thickness of the pipe is assumed to be 1.0 cm. If the crack is, for example, 0.57 centimeters deep $[0.57 = (1-\delta) = (1-0.43)$ cm$]$ then when a frequency of about $10^4$ is reached, current will no longer be flowing through the crack and normal impedance for that frequency will be detected. At frequencies below $10^4$ hertz the crack will increase impedance.

Figure 6:
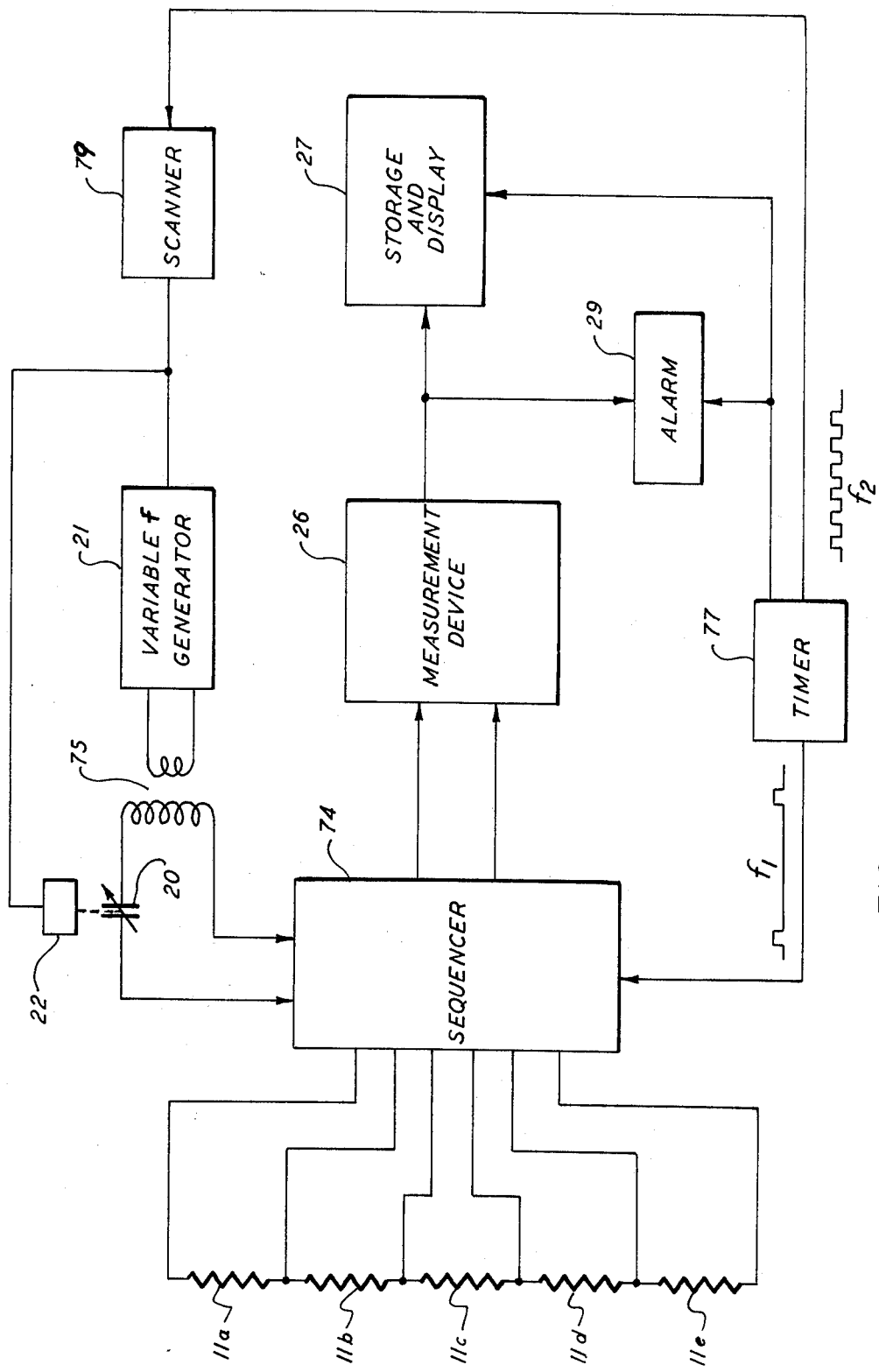
FIG. 6 is a block diagram of a system according to the present invention for measuring a plurality of pipe sections in sequence.

There are, of course, numerous pipe sections which must be monitored in a device such a nuclear reactor or in a petrochemical system. In order to avoid gross duplication of equipment the present invention employs sequencing arrangement to check, in sequence, each of the various sections over a predetermined period of time. As an example a number of resistances designated 11a through 11e are shown on FIG. 6. Each represents a section of pipe or a group of sections of pipes such as shown on FIGS. 2 and 3. Connections are made at the two ends of each section of pipe being monitored, i.e. connections such as the clamps 13 of FIG. 1. The leads from these clamps connect to a sequencer 74. The sequencer can be made using conventional techniques and may comprise, for example, a plurality of relays actuated by a stepper switch. As an input to the sequencer the secondary of a transformer 75 is shown having its primary coupled to the variable frequency generator 21. Because of the high currents required a stepdown of voltage and a stepup of current in such a transformer becomes particularly practical. Shown is a timer 77. Timer 77 may simply comprise a clock and a plurality of counting stages, the clock outputting two separate frequencies. A frequency $f1$ is provided which is a low frequency, for example, one pulse per minute. This frequency is used to advance the sequencer 74. In other words, each pulse causes the stepper switch therein to advance once to examine a new section of pipe. The second frequency output of the timer 77 is a frequency $f2$ considerably higher than the frequency $f1$. For example, it may be a pulse every second or every 5 seconds. Frequency $f2$ is an input to a scanner 79, which may also be stepper switch or the like, and the output of which is used to step the variable frequency generator 21 through the frequency range. For example, it might step the variable frequency generator through the frequencies of 1 Hz to $10^8$ as shown in Table I. Preferably, frequencies providing skin depth steps on the order of 0.1mm will be preselected for measuring. i.e. for a 1cm thick pipe steps of about 100 Hz between 100 and $10^6$Hz. Thus, for each of the positions of the sequencer 74 the generator 21 steps through all of the preselected frequencies. These outputs are also used to switch capacitor 20 via switching means 22 when operating using the resonance method. Outputs are also taken off from the sequencer 74 and provided to the measurement device 26 which can be the impedance measurement device in FIG. 1 or the current and voltage measurement devices 24 and 25' of FIG. 4. In the case of a bridge measurement, the impedances 11a and 11b can be coupled in the circuit first, then the impedances 11b and 11c and so on. Alternatively, the impedances 11a and 11b can first be measured and then the impedances 11c and 11d. Outputs from the timer 77 are also provided to the storage and display which, as noted above, may be a chart recorder, i.e. a strip recorder. These outputs will result in a sequencing of the output channels thereon to permit individually monitoring each of the impedances. Since on the chart recorder the various frequencies will be evident, one strip can be used for each pipe section if desired, i.e. switching need not take place for each separate frequency. However, the alarm 29 as described above must be indexed for each of the frequencies because of the variation in resistance as shown in Table I. Thus, the frequency $f2$ must be provided to the alarm 29 so that a comparison is properly made between the measured values and the previously stored values for that frequency.

The sequencer 74 must switch high currents and thus must be constructed using relays or switches of relatively high capacity. However, the switching between the impedance measurement and the storage and display and the alarm will be switching at low voltages and low currents. Implementation of this part of the system can be carried out using readily available data acquisition equipment, for example, the Hewlett Packard automatic data acquisition system, model 3050B. This includes a scanner and digital multimeter and can easily be interfaced with a strip or chart recorder.

FIG. 7 illustrates a further embodiment of the present invention utilizing a transmitter and receiver. In the illustrated embodiment a transmitter 101 is coupled to one portion of the pipe 11 and a receiver 103 a distance therefrom. Also shown is another receiver 105 coupled to the same input lead 107 by means of which a transmitter is coupled to the pipe 11. A line 109 from the transmitter and labeled blanking is provided into the receiver. In an arrangement of this nature various modes of operation are possible. The transmitter can be a conventional fm transmitter operating with a carrier frequency in the megacycle range and frequency modulated to cause currents to flow over the full thickness of the pipe 11 at various skin depths. The receiver 103 will then be tunable to the various modulation frequencies to measure amplitudes at each of the various frequencies to give an indication of current flowing therein. As with the previous embodiments, a crack between the transmitter and receiver will result in increased resistance and attenuation of the amplitude of the detected signal depending on the frequency and thus on the skin depth.

Alternatively, the transmitter can be a microwave transmitter and the pipe 11 used as a dielectric wave guide. Such an arrangement is particularly useful in detecting cracks beginning on the inside. The high frequency energy which will be guided along the inside surface of the pipe will be disturbed by any cracks occuring therein and such disturbances can be detected at the receiver. Both at this frequency and at lower frequencies pulsed forms of transmission can be used. In fact, it is even possible to use the transmitter to transmit a simple square pulse along the pipe 11. Such pulsed energy may be detected by the receiver 103 to determine its transmission characteristics which will be affected by any internal cracks. However, the receiver 105 may also be used to detect reflections of such pulse energy. In conventional fashion the blanking output on line 109 blanks the receiver input during transmission so that it will not receive the pulse being transmitted. However, once the transmission is finished the blanking signal is removed and the receiver can receive any reflections caused by internal cracks.

FIG. 8 illustrates an arrangement which is particularly useful in long pipe lines. This is a coaxial arrangement in which the connections are almost identical of the pipe heating system disclosed in Kirk-Othmer, Encyclopedia of Chemical Technology, Supplement pp. 694 et seq, particularly FIGS. 6 and 7 of p. 706. In essence, the arrangement shown therein can be used as the section of pipe to be measured and the generator and measuring means coupled thereacross. Such an arrangement is illustrated generally on FIG. 8. Shown are the lines 17 and 19 which will be coupled to the generator and measuring means in the manner described above. The line 17 is coupled to the inner surface of the pipe 11. The line 19 is connected to a conductor 115 disposed inside the pipe 11 and brought out a suitable feed through. Conductor 115 may be disposed as illustrated using the supports 117 but may also be disposed so that it lies against the side or bottom of the pipe. The internal conductor 115 is electrically connected to the internal surface of the pipe with a connection 119. In this embodiment, current flows out on one of the conductors, i.e. the internal conductor 115 or the pipe 11 and back on the other. Because of this arrangement, the magnetic fields which occur cause the skin effect to force the current toward the inner surface of the pipe. This results in the ability to easily detect cracks and other defects which occur at the internal surface. In pipe lines, particularly those carrying materials which are corrosive, this is where most defects can be expected to occur. All of the measuring methods and means disclosed above in connection with FIGS. 1,2,4, and 6 can equally well be used with this embodiment.

Although the present invention has been disclosed in connection with pipes it can also be applied to other hollow structures where a similar skin effect will be found. For example, it can be used for monitoring hollow helicopter rotors.

Thus, an improved method of detecting metal failures in situ has been shown and described. Although specific embodiments have been illustrated and described, it will be obvious to those skilled in the art that various modifications may be made without departing from the spirit which is intended to be limited solely by the appended claims.

I claim:

1. A method of detecting metal failures in situ comprising:
   a. conductively coupling an electrical generator to a section of metal to be tested to form a closed conductive circuit;
   b. passing currents at different frequencies through said section of metal to be tested;
   c. measuring at least one electrical characteristic of the circuit at each of said different frequencies; and
   d. comparing said at least one characteristic with a previous value of that characteristic whereby the presence and depth of a failure in said metal can be detected by determining the frequencies at which a change in said characteristic is found.

2. The method according to claim 1 wherein said section of metal to be detected is a section of pipe.

3. The method according to claim 1 wherein said at least one characteristic is impedance.

4. The method according to claim 3 wherein said impedance measurement is made using an impedance bridge, said section of pipe to be measured forming one arm of said bridge and further including establishing a reference arm of said bridge which is at the same temperature as said pipe.

5. The method according to claim 4 where said reference arm of said bridge comprises a second section of pipe in the same piping system.

6. The method according to claim 2 wherein a large plurality of pipe sections are to be measured and further including the step of sequentially applying said currents at different frequencies to each section and measuring the impedance of each section.

7. The method according to claim 1 wherein:
   a. said at least one characteristic is current;
   b. a variable capacitor is placed in the circuit made up of said generator and said section of metal;
   c. said generator is operated with a pre-established fixed voltage for each frequency;
   d. said previous value is established by tuning said capacitor for resonance with said section known to be without failure and measuring the current as the characteristic.

8. The method of claim 7 wherein said capacitor is in series with said section of metal.

9. The method of claim 7 wherein said capacitor is in parallel with said section of metal.

10. The method according to claim 1 wherein:
   a. a variable capacitor is placed in the circuit made up of said generator and said section of metal;
   b. said at least one characteristic is the voltage across said capacitor;
   c. said generator is operated with pre-established fixed voltage for each frequency; and
   d. said previous value is established by tuning said capacitor for resonance with said section known to be without failure and measuring the voltage across said capacitor.

11. The method of claim 1 wherein said at least one characteristic is resonance.

12. The method according to claim 11 and further including:
   a. placing a variable capacitor in the circuit with said section of metal;
   b. determining a value of capacitance resulting in resonance at each frequency; and
   c. measuring, with each of said capacitors in the circuit, the resonance frequency by varying the frequency output of said generator near the resonance frequency.

13. The method of claim 1 wherein the characteristic measured is a characteristic associated with transmission, said generator being coupled to said section as a transmitter.

14. The method according to claim 1 wherein said at least one characteristic is the Q of the circuit.

15. The method according to claim 1 wherein said section of metal is a section of pipeline and further including the step of disposing a conductor within said pipeline, one end of said conductor coupled to said pipeline and coupling said electrical generator to said pipeline and to the other end of said conductor.

16. Apparatus for detecting metal failures in situ comprising:
   a. generating means for providing output currents and voltages at different frequencies;
   b. means conductively coupling the output of said generating means across a section of metal to be tested to form a closed conducting circuit; and
   c. means for measuring an electrical characteristic of said circuit for each of a plurality of frequencies output by said generating means.

17. Apparatus according to claim 16 wherein said section of metal to be tested comprises a section of pipe.

18. Apparatus according to claim 17 wherein said characteristic is impedance and said measurement means comprise an impedance bridge.

19. Apparatus according to claim 18 wherein said section of pipe comprises one arm of said bridge and further including means for providing reference impedance in another arm of said bridge having essentially the same impedance and maintained at the same temperature as said section of pipe.

20. Apparatus according to claim 19 wherein said reference arm of said bridge comprises another section of pipe.

21. Apparatus according to claim 19 wherein said section of pipe comprises a plurality of branches in a piping system, each branch representing a separate impedance.

22. Apparatus according to claim 16 and further including means for storing and displaying the output of said measuring means.

23. Apparatus according to claim 16 and further including alarm means responsive to the output of said measuring means.

24. Apparatus according to claim 16 and wherein a plurality of sections are to be measured and further including means for sequentially applying the output of said generating means to each of said sections and sequentially coupling said measuring means to each of said sections therewith.

25. Apparatus according to claim 24 and further including means for automatically operating said sequencer and for automatically causing said generating means to step through a plurality of frequencies.

26. Apparatus according to claim 17 wherein said section of pipe comprises a portion of the piping in a nuclear reactor.

27. Apparatus according to claim 17 wherein said section of pipe comprises a portion of the piping system of a petrochemical installation.

28. Apparatus according to claim 17 wherein said section of pipe comprises a portion of an elongated pipeline.

29. Apparatus according to claim 17 and further including a conductor disposed within said section of pipe, said conductor having one end coupled to said pipe with said means for providing output currents and voltages at different frequencies coupled the other end of said conductor and to said pipe proximate to said location of the other end of said conductor.

30. Apparatus according to claim 16 and further including means to compare said measured value with a previous value.

31. Apparatus according to claim 16 wherein said characteristic is current and further including means for coupling to said circuit, for each frequency, a capacitor which will result in resonance at that frequency.

32. Apparatus according to claim 16 wherein said generating means comprises a transmitter and said measuring means a receiver.

33. Apparatus according to claim 16 wherein said means for measuring comprises a Q meter.

34. Apparatus according to claim 16 wherein said means for measuring comprises a voltmeter.

35. Apparatus according to claim 34 wherein said volt meter is a digital volt meter.

36. Apparatus according to claim 34 and further including means for coupling a capacitor into said circuit, said characteristic being the voltage across said capacitor and wherein said voltmeter is coupled across said capacitor.

* * * * *